United States Patent
Shin et al.

(10) Patent No.: US 9,927,425 B2
(45) Date of Patent: Mar. 27, 2018

(54) APPARATUS AND METHOD FOR TESTING MULTI-FUNCTION AND DRUG RESPONSE OF CENTRIFUGAL MICROFLUIDIC-BASED PLATELETS

(71) Applicant: Korea University Research and Business Foundation, Seoul (KR)

(72) Inventors: Se Hyun Shin, Seoul (KR); Chae Seung Lim, Anyang-si (KR); Jeong Hoon Nam, Seoul (KR); Hyun Jung Lim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 211 days.

(21) Appl. No.: 14/758,291

(22) PCT Filed: Dec. 27, 2013

(86) PCT No.: PCT/KR2013/012289
§ 371 (c)(1),
(2) Date: Jun. 29, 2015

(87) PCT Pub. No.: WO2014/104807
PCT Pub. Date: Jul. 3, 2014

(65) Prior Publication Data
US 2015/0355167 A1    Dec. 10, 2015

(30) Foreign Application Priority Data

Dec. 31, 2012  (KR) .................. 10-2012-0158117

(51) Int. Cl.
*G01N 33/86*  (2006.01)
*G01N 33/50*  (2006.01)
(Continued)

(52) U.S. Cl.
CPC ..... *G01N 33/5029* (2013.01); *B01F 13/0059* (2013.01); *B01F 13/0818* (2013.01);
(Continued)

(58) Field of Classification Search
CPC ......... B01F 15/0233; B01L 2300/0803; B01L 2400/0409; G01N 35/00069
See application file for complete search history.

(56) References Cited

U.S. PATENT DOCUMENTS 3,854,324 A * 12/1974 Altshuler ........... G01N 33/4905
                                                          436/69
5,447,440 A *  9/1995 Davis ..................... G01N 11/04
                                                          422/73
(Continued)

FOREIGN PATENT DOCUMENTS

KR    10-2011-0056168      5/2011
KR    10-1193566 B1       10/2012

OTHER PUBLICATIONS

International Search Report dated Apr. 8, 2014, in counterpart International Application No. PCT/KR2013/012289 (2 pages in English, 2 pages in Korea.

*Primary Examiner* — Paul S Hyun
(74) *Attorney, Agent, or Firm* — NSIP Law (57) ABSTRACT

The present invention relates to an apparatus and method for testing a multi-function and a drug response of platelet based on a centrifugal microfluidics. The testing apparatus according to the present invention may include: a rotatable disk; a sample chamber arranged at the center of the disk such that a blood sample is accommodated therein; stirring chambers respectively connected to the sample chamber in multiple radial directions so as to introduce a shear flow in the blood sample; microchannels connected to the stirring chambers such that adhesion and cohesion of platelets occur during the movement of the blood sample; and a waste sample chamber (Continued)

in which the blood sample is accommodated after passing through the microchannels. According to the present invention, multiple drug tests can be performed on a single blood sample at one time in multiple channels such that multiple tests is possible with respect to complex platelet functions, and thus testing time is reduced and testing costs can be saved.

19 Claims, 4 Drawing Sheets

(51) Int. Cl.
    *G01N 33/49*      (2006.01)
    *B01L 3/00*      (2006.01)
    *B01F 13/00*      (2006.01)
    *B01F 13/08*      (2006.01)
    *B01F 15/02*      (2006.01)
    *G01N 35/00*      (2006.01)

(52) U.S. Cl.
    CPC .... *B01F 15/0233* (2013.01); *B01L 3/502746* (2013.01); *G01N 33/491* (2013.01); *G01N 33/5044* (2013.01); *B01L 2300/0803* (2013.01); *B01L 2300/087* (2013.01); *B01L 2300/0883* (2013.01); *B01L 2400/0409* (2013.01); *B01L 2400/0677* (2013.01); *G01N 35/00069* (2013.01); *G01N 2035/00237* (2013.01)

(56) References Cited

U.S. PATENT DOCUMENTS

| | | | | |
|---|---|---|---|---|
| 6,438,498 | B1* | 8/2002 | Opalsky | B01L 3/5027 |
| | | | | 435/6.11 |
| 7,261,861 | B2* | 8/2007 | Kautzky | G01N 33/4905 |
| | | | | 422/73 |
| 2008/0056949 | A1* | 3/2008 | Lee | B01L 3/50273 |
| | | | | 422/72 |
| 2009/0227041 | A1* | 9/2009 | Wang | G01N 35/00069 |
| | | | | 436/180 |
| 2010/0099130 | A1 | 4/2010 | Haworth et al. | |
| 2011/0223627 | A1 | 9/2011 | Neeves et al. | |
| 2012/0301966 | A1 | 11/2012 | Hosokawa et al. | |
| 2013/0171697 | A1* | 7/2013 | Park | C12N 1/08 |
| | | | | 435/91.2 |

* cited by examiner

APPARATUS AND METHOD FOR TESTING MULTI-FUNCTION AND DRUG RESPONSE OF CENTRIFUGAL MICROFLUIDIC-BASED PLATELETS

CROSS-REFERENCE TO RELATED APPLICATIONS

This application is a U.S. National Stage Application of International Application No. PCT/KR2013/012289, filed on Dec. 27, 2013, which claims the benefit under 35 USC 119(a) and 365(b) of Korean Patent Application No. 10-2012-0158117, filed on Dec. 31, 2012, in the Korean Intellectual Property Office.

TECHNICAL FIELD

The invention relates to an apparatus and method for testing drug response of a platelet and in particular to an apparatus and method for testing a multifunction and a drug response of a platelet based on a centrifugal microfluidics such that various test can be carried out automatically with a small amount of blood using microfluidics on a disposable rotating disk for early diagnosis of thrombotic ischemia and bleeders' disease.

BACKGROUND ART

Thrombosis is the formation of a hemostasis or a blood clot inside a blood vessel. Thrombosis in coronary artery of the heart or cerebrovascular part causes a heart attack or cerebral infarction. Thrombosis referred to as silent killer is becoming the main cause of death for our contemporaries. The problem is that thrombosis or bleeding disease is not caused by genetic defect only and cause thereof is not discovered clearly.

More seriously, thrombosis prevalence rate is fast increasing due to genetic defect and acquired factors. Therefore, an apparatus and method have been required to make a quantitative test for thrombosis or bleeding disease and to carry out an early diagnosis and prognosis decision.

There are many factors which play roles in hemostasis at vascular injury sites. All of biochemical and biological mechanism of each factor play a critical role and hemostasis of a platelet plays the most crucial role. A platelet is not attached to the arterial walls at no injury sites, but biochemical and biological mechanism is activated at vascular injury sites, thereby hemostasis is achieved regardless of flow conditions.

Many method and devices have been developed to subdivide and test a platelet function. A platelet function test is an important test to discern bleeding disorders which are caused by a congenital or acquired disorder of platelet function in case of the bleeding disorders having no numerical platelet disorder. Also, this platelet function test is being used to examine an increase of hemorrhage tendency or a drug-tolerance which is caused by antiplatelet agent used for the treatment or prevention of cardiovascular disorders.

If there is an injury at endothelioid cells in the blood vessel, an inner material in the endothelioid such as collagen is exposed to the blood and a platelet is attached to the material and is activated. Attachment mechanism of platelet has different characteristics depending on blood flow conditions.

In particular, if a blood flow rate is high in the artery and a shear stress applied to the blood vessel wall is high, platelet is not attached to the inner membrane of the blood vessel easily. In this condition, von Willebrand factor (vWF) is activated and is easily attached to the wall of the blood vessel and a platelet is attached to the wall of the blood vessel by vWF. Of course, it is known that a glycoproteic receptor complex such as GPIb-IX-V which is contained in the platelet cell membrane induces the reaction with vWF, leading to the attachment.

As such, an attached platelet induces an aggregation by attracting the same kind of platelet and leads to hemostasis. Then, hemostasis is reinforced by fibrin.

However, the function of platelet is not always favorable, but can produce adverse effect in a certain flow condition or situation. For example, when the blood vessel wall became narrow locally by artery hardening, a platelet passing through this narrow part is exposed to a high shear ratio and is activated, and then adhesion and aggregation occurs in the rear of the narrow part and leads to thrombosis which blocks the blood vessel.

As explained above, a platelet and vWF are activated by the size of a blood flow, i.e., a shear stress the flow, thereby leading to the increase of an adhesive property and the generation of hemostasis. It is known that the shear stress required for the activation of a platelet or vWF is at least 8 Pa and the shear rate is at least 5,000 l/s.

As such, various devices are suggested and developed for an early diagnosis and prognosis test of hemostasis or bleeding disease and they can be divided into an electric method, an optical method, a time measuring method to stop bleeding, etc., based on the measuring sensor.

A bleeding time (BT) method was developed about 100 years ago which measures a bleeding time and is still being used for a screening test of a platelet function. However, a current platelet function test has problems such as a difficult standardization, a low diagnostic validity and a use of invasive technique and therefore an objectified measuring method to measure a platelet function has been required.

To solve the problems, a platelet function analyzer (e.g.: PFA-100) is developed which is being used to measure a platelet function. This analyzer uses a feature that a platelet is aggregated by activated vWF in a high shear rate. To measure this feature, after whole blood flows in a long capillary tube, a platelet aggregates in an orifice coated by ADP or epinephrine together with collagen and then time by which the orifice is blocked is measure by pressure, flow rate, etc.

This platelet function test strictly depends on the function of vWF. This test has disadvantages that the test depends on hematocrit (Hct) and an antiplatelet test such as a test using aspirin or clopidogrel is not possible. Also, disadvantageously, two step tests are required for the function test of platelet and cost for the test is increasing.

In particular, to activate vWF, a blood sample must be exposed for a predetermined time with a high shear rate. For this, PFA-100 uses a method for making blood flow at high speed in a long capillary tube. However, disadvantageously, this method requires a large quantity of blood. Also, it is a disadvantage that vWF is not activated at the center of the capillary tube where a shear rate is minimum while vWF is activated near the tube wall where a shear rate is maximum, thereby a repeatability of test results is not guaranteed.

IMPACT of Diamed Co., Ltd. Uses a rotation-type Couette flow in the form of Cone-Plate. In this method, a uniform shear stress is applied to the blood contained therein and an attachment degree of platelet is measured when a high shear stress is applied. Like PFA-100, this method has a disadvantage that it depends too much on the concentration and function of fibrinogen and vWF.

Verify-NOW (Accumetrics) uses a method to measure an aggregation degree of platelet by a turbidity using a optical sensor. In this method, an agonist is mixed with blood and then a microbead on which collagen is coated is reacted so that a platelet in the blood is aggregated. Then, turbidity is measured over time. The frequency of use this method is being increased recently, but this method still has disadvantages of prior methods to measure a turbidity.

DISCLOSURE OF THE INVENTION

Technical Problem

An object of the present invention is to solve the above problems and the present invention provides an apparatus and method for testing multifunction and drug-response of a platelet based on a centrifugal microfluidics by which it is possible to make a multiple test including early diagnosis and prognosis of bleeding disease and thrombosis with a single test, thereby saving test costs and increasing a repeatability and an accuracy of test.

Another object of the present invention is to provide an apparatus and method for testing multifunction and drug-response of a platelet based on a centrifugal microfluidics by which a closure time of a blood flow can be measured automatically.

Technical Solution

To achieve the above object, the invention provides an apparatus for testing a multifunction and a drug response of a platelet based on a centrifugal microfluidics comprising: a rotatable disk; a sample chamber which is located in the center of the disk and which contains a blood sample therein; stirring chambers which are connected to the sample chamber in a radial direction, respectively and which induce a shear flow in the blood sample; microchannels which are connected to the stirring chambers and in which aggregation and adhesion of a platelet occur during a migration of the blood sample; and waste sample chambers to receive the blood sample which passed the microchannels.

The apparatus according to the invention further comprises a measuring part which is installed on the disk and which measures a migration distance of the blood sample.

A stirrer is rotatably installed in the stirring chamber.

The stirrer is shaped in the form chosen from a straight cylindrical bar, a cross cylindrical bar and a circular plate.

A drug which activates or inactivates an aggregation of a platelet is contained in the stirrer in a liquid or solid state.

The drug is at least one agonist chosen from collagen, adenosine diphosphate (ADP) and epinephrine.

The drug is at least one antagonist chosen from aspirin, P2Y1 receptor antagonist and P2Y12 receptor antagonist.

The P2Y1 receptor antagonist is at least one chosen from MRS 2179, MRS 2279, MRS 2500, A2P5P, A3P5P and A3P5PS.

The P2Y12 receptor antagonist is at least one chosen from clopidogrel, ticlopidine, prasugrel, AR-C67085MX, cangrelor, C1330-7, MRS 2395 and 2-methylthioadenosine-5'-monophosphate.

A minimum shear rate in the shear flow generated by the stirrer is at least 5,000 $(s^{-1})$ or a minimum shear stress is at least 8 Pa.

A center and both sides of the stirrer are open and the open portion is provided with a seal.

The seal is a phase-change material or an aqueous membrane.

The phase-change material is paraffin wax and the aqueous membrane is starch.

A microfluidic valve is installed in the front part of the microchannel to control the flow of the blood sample.

The microchannel is shaped in the form of at least one of a straight line, a curve or a zigzag, or the combination thereof.

A plurality of the intermediate chambers is formed at a plurality of points in the straight channel.

The microchannel is provided with a plurality of expansion parts which are relatively wide.

Also, the invention provides an apparatus for testing a multifunction and a drug response of a platelet based on a centrifugal microfluidics comprising: a rotatable disk; stirring chambers which are arranged on the center of the disk circumferentially, which contain a blood sample, respectively and which induce shear flow in the blood sample; microchannels which are connected to the stirring chambers and in which aggregation and adhesion of a platelet occur during a migration of the blood sample; and waste sample chambers to receive the blood sample which passed through the microchannels.

Further, the invention provides a method for testing a multifunction and a drug response of a platelet based on a centrifugal microfluidics comprising the following steps: introducing a blood sample; entering the blood sample into a stirring chamber and discharging a drug into the stirring chamber by the rotation of a stirrer in the stirring chamber; rotating a disk on which a stirring chamber is installed; migrating the blood sample through a microchannel and stopping the blood sample by an aggregation of a platelet; and stopping the disk and measuring a migration degree of the blood sample.

Moreover, the invention provides a method for testing a multifunction and a drug response of a platelet based on a centrifugal microfluidics comprising the following steps: introducing a blood sample; rotating a disk into which the blood sample was introduced; migrating the blood sample discharged through a microchannel and stopping the blood sample by an aggregation of a platelet; and stopping the disk and measuring a migration degree of the blood sample.

Advantageous Effect

According to the invention, it is possible to make a single test for a large quantity of blood sample through a plurality of channels quickly.

Also, with a single test only, it is possible to make a multiple test regarding a complex platelet function by performing a multiple drug tests for a single blood sample in a plurality of channels, thereby saving time and cost for a test.

Further, a driving device to migrate blood such as a vacuum pump, etc., is not needed, but is replaced with the use of a centrifugal force.

Further, elements which will be in contact with blood can be made of disposable and be discarded after use. Therefore, it is easy to use and avoid a blood-borne infection.

Further, it is easy to make a bulk test by means of a system having a short measuring time and enabling a simultaneous test on various samples.

MODE FOR CARRYING OUT THE INVENTION

Hereinafter, an embodiment of an apparatus for testing multi-function and drug response of platelet based on a centrifugal microfluidics according to the invention will be described in detail referring to the attached drawings.

Figure 1:
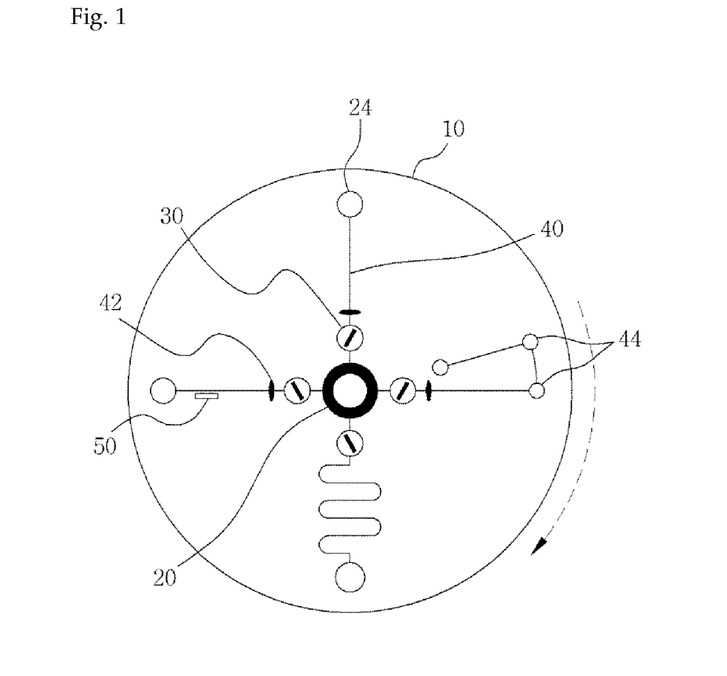
FIG. 1 shows an apparatus for testing a multi-function and a drug response of a platelet based on a centrifugal microfluidics according to one embodiment of the present invention.
Figure 2:
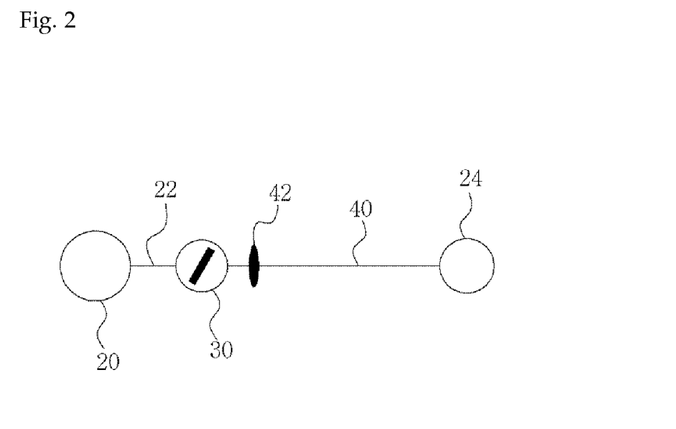
FIG. 2 shows a process of a blood sample according to one embodiment of the present invention.
Figure 3:
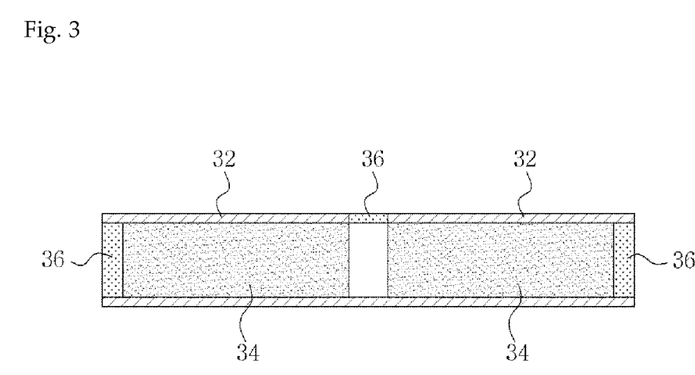
FIG. 3 shows an inner part of a stirrer according to one embodiment of the present invention.

FIG. 1 shows an arrangement of an apparatus for testing multi-function and drug response of a platelet based on a centrifugal microfluidics according to one embodiment of the invention. FIG. 2 shows a process of the blood sample according to one embodiment of the invention. FIG. 3 shows an inner part of a stirrer according to one embodiment of the invention.

As shown in the figures, the apparatus for testing multi-function and drug response of platelet based on a centrifugal microfluidics according to the invention comprises a rotatable disk 10; a sample chamber 20 which is located at the center of the disk and which contains a blood sample therein; stirring chambers 30 which are connected to the sample chamber in a radial direction, respectively and which introduce a shear flow in the blood sample; microchannels 40 which are connected to the stirring chambers 30 and in which adhesion and aggregation of platelet occur; and waste sample chambers 24 which receive the blood sample which passed through the microchannels 40.

The microchannel 40 may have a cross section which is in the form of a polygon such as a rectangle, a circle or an oval. For example, in case of a cross section of a square, the length of a side may be in the range of 1 to 1,000 μm, preferably 10 to 200 μm, more preferably 20 to 50 μm. In case of a cross section of a circle, the diameter may have the same dimension range as above.

In one embodiment, when the disk 10 which is disposable rotates, the blood sample migrates in a radial direction by a centrifugal force. In this case, the migration distance of the sample differs depending on the aggregation and adhesion of a platelet and the relative aggregation and adhesion of a platelet are measured by the difference of the migration distances.

FIG. 1 represents one embodiment of the invention. A plurality of stirring chambers 30 is disposed circumferentially with respect to one blood sample chamber 10. Each stirring chamber 30 contains a specific test drug and various tests for a drug response can be performed with a single test. Here, the measurement of the migration distance of a blood sample is carried out by a measuring part 50 disposed on the disk 10. The measuring part 50 may be configured as a micro camera to obtain and analyze an image or may be configured as the combination of sensors such as a photodiode sensor and LED at a specific location to measure the migration distance of a blood sample Referring to FIG. 2, a blood sample is supplied to the sample chamber 20 and then the blood sample is introduced into the stirring chamber 30 by means of a connection channel 22. Here, to prevent the blood sample from migrating downstream, a microfluidic valve 42 is installed in the front part of the microchannel 40. Then, the blood sample is introduced into a waste sample chamber 24 through the microchannel 40.

Referring to FIG. 3, a stirrer 32 is rotatably installed in the stirring chamber 30 to stir the blood sample. The stirrer 32 may rotate in a non-contact manner such as a magnetic force and may effectively generate a stirring and a shear flow by the control of rpm.

Also, the stirrer 32 may have various shapes such as a straight cylindrical bar which is being used generally, a cross cylindrical bar or a circular plate, etc. When the stirrer 32 rotates by a non-contact force, a stirring as well as a shear flow depending on rpm occur in the stirring chamber 30. The shear flow can be an intermittent shear flow for a straight cylindrical bar or can be a continuous shear flow for a circular plate. For example, the stirrer 32 can be made of a thin metal such that it can be magnetized by the magnetic force of a separate a stir-inducing device (not shown) and be influenced without a mechanical connection.

Preferably, the diameter or thickness of the stirrer 32 may be half of the depth of the stirring chamber 30 and the length or diameter of the stirrer 32 may be 80 to 90% of the diameter of the stirring chamber 30.

Meanwhile, the drug 34 to activate or inactivate the aggregation of a platelet is stored in the stirrer 34 in a liquid state or a solid state. That is, the stirrer 32 can be hollow and the drug in liquid form or in particle powder form can be stored in the stirrer 34.

In one example, for the stirrer 32 in the form of a straight cylindrical bar, the center and both sides of the stirrer 32 are open and the open portion is provided with a seal 36. Preferably, the seal 36 can be a phase-change material such as paraffin wax or an aqueous membrane such as starch. Paraffin wax changes a phase from solid to liquid when it is exposed to a predetermined temperature and the sealing of the stirrer 32 is removed. At this time, the drug 34 in the stirrer 32 is discharged into the stirring chamber 30 by a centrifugal force. Also, starch melts easily when it is exposed to blood and the sealing is removed so that the drug 34 is discharged into the stirring chamber 30.

Also, in case that the seal 36 of the phase-change material is used, the application of a laser or an electromagnetic wave to the seal 36 causes the phase-change material to be heated and melt away, so that the seal is removed. Further, in case that the seal 36 of the aqueous membrane is used, the rotation of the stirrer 32 to facilitate the melting in the blood causes the seal to be removed so that the drug 34 in the stirrer 34 is discharged. As such, regarding the discharge of the drug 34, a centrifugal force by the rotation of the stirrer 32 can be a main driving force.

To test whether a platelet is activated by a mechanical force, it is preferable that the minimum shear rate by the rotation of the stirrer 32 is at least 5,000 $(s^{-1})$ or that the minimum shear stress is at least 8 Pa. Also, it is preferable that the time for which the blood sample is exposed to the shear flow field is at least 30 seconds. This is to achieve a sufficient activation of a platelet and von Willebrand factor (vWF) by using the shear rate.

The drug 34 which is filled in the stirrer 32 may be an agonist which activates aggregation of a platelet such as adenosine diphosphate (ADP), epinephrine, etc., an antagonist which deactivates aggregation or adhesion of a platelet, or the combination thereof.

Also, the drug 34 can be filled in the stirrer 32 in the form of liquid and liquid and in the form of liquid and solid, respectively and it can be divided into separate spaces and stored therein. Moreover, when the drug 34 is filled in the form of solid only, fine particles can be mixed each other and stored.

As such, if the drug 34 is discharged from the stirrer 32 and then is introduced into a blood sample, the drug is mixed uniformly by the rotation of the stirrer 32 and a platelet response by the drug 34 occurs. In particular, if the drug is an agonist, the aggregation of a platelet is facilitated such that big aggregates are formed.

If the mixing of the drug 34 and the blood sample is completed by the stirrer 32, the rotating device (not shown) connected to the disk 10 which comprises the stirring chamber 30, the microchannel 40, etc. begins to rotate gradually and rotates at a predetermined rpm. Here, the blood sample contained in the stirring chamber 30 tries to be discharged in a radial direction by a centrifugal force. But, the stirring chamber is clogged with a seal 36 such as a phase-change material and therefore, the flow is prevented. However, if heat is transferred to the phase-change material by means of an electromagnetic wave, a laser or other heating means, a flow path is opened and then the blood sample migrates in a radial direction.

Turning to FIGS. 1 and 2, when a mixing of the drug 34 and a shear stirring are completed, the microfluidic valve 42 is opened and the disk 10 rotates. At this time, a force is applied to blood sample in a radial direction by a centrifugal force of the rotation and the blood sample migrates along the microchannel 40. Here, a migration speed of the blood sample which reacted with the drug 34 differs depending on the aggregation degree of a platelet and hence, a migration distance differs. Based on these features, a drug-response test for a platelet is carried out.

The progress of the blood sample is stopped in the microchannel 40 by the aggregation of a platelet. At this time, a migration ratio of the blood sample can be measured relatively. Also, in another example for the microchannel 40, as shown in FIG. 1, the intermediate chamber 44 is formed at a plurality of points in the straight channel. The intermediate chamber 44 decreases a flow rate of the blood sample to induce aggregation of a platelet and facilitates the clogging of the aggregated platelet when the aggregated platelet enters into the microchannel 40 again.

In the microchannel 40 which is connected to the stirring chamber 30 and which comprises a plurality of intermediate chambers 44, the blood migration degree can be determined depending on the drug-response degree of blood. That is, the blood sample which responds well to an agonist forms a number of big platelet aggregates and this aggregates cause a substantial flow resistance to the microchannel 40 to decrease the migration ratio of the blood to control group. However, the blood sample which does not respond well to an agonist has a low degree of platelet aggregation and thus the migration distance of blood can be increased significantly such that the blood sample can migrate to the lower course by a centrifugal force. As such, the migration degree of blood sample which is mixed with a drug 34 can be compared with the migration distance of control group to measure the migration ratio.

Further, the microchannel 40 is located downstream from the stirring chamber 30 and the microchannel is arranged in a radial direction in the form of a straight line, a curve or a zigzag, or the combination thereof, as shown in FIG. 1.

The microchannel 40 can be arranged in the form of a straight line channel. Alternatively, referring to FIG. 4, the microchannel is provided with an expansion part 46 which is relatively wide to decrease the flow rate of blood sample and to increase the aggregation and adhesion of a platelet. If the expansion part 46 is arranged appropriately in the middle of the microchannel, the blood sample will have features that it migrates with a pulsed pressure and a shear stress and the flow in the body can be simulated. The microchannel 40 connected to the expansion part 46 may describe a stenosis in the blood vessel.

Figure 4:
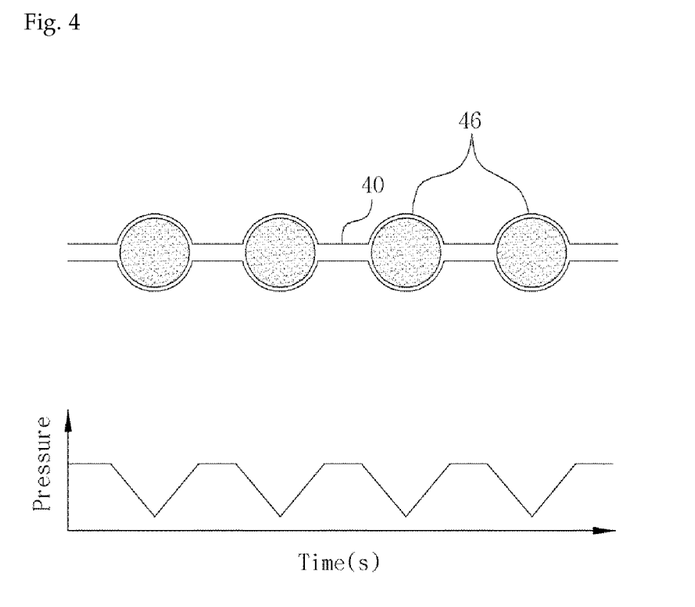
FIG. 4 shows another example of a microchannel and its flow pressure distribution according to one embodiment of the present invention.

Also, the expansion part 46 has a surface on which an agonist is coated to increase the adhesion of a platelet such that the migration degree of blood can be discriminated more easily. The blood sample which passed through the microchannel 40 is collected at the waste sample chamber 24.

Regarding the drug, an agonist such as collagen, ADP, epinephrine, etc. may be used to facilitate the adhesion of a platelet, or an antagonist such as aspirin, P2Y1 receptor antagonist, P2Y12 receptor antagonist, etc. may be used to interrupt or restrain the aggregation of a platelet.

P2Y1 receptor antagonist may be chosen from at least one of MRS 2179, MRS 2279, MRS 2500, A2P5P, A3P5P, A3P5PS, etc. P2Y12 receptor antagonist may be chosen from at least one of clopidogrel, ticlopidine, prasugrel, AR-C67085MX, cangrelor, C1330-7, MRS 2395, 2-methylthioadenosine-5'-monophosphate, etc.

In particular, for a taker who took the above drugs, the aggregation function of the platelet and the resistance to the drugs can be measured by the test apparatus according to the invention.

For the measurement of the function of the platelet, blood from a normal person or a taker who took aspirin and clopidogrel is collected in citrated tubes. Then, 50 to 100 microliter of whole blood is taken and is reacted at 37° C. for 10 to 30 minutes using optimum concentration of ADP, prostaglandin E, fibrinogen and arachidonic acid, respectively. After the reaction, blood is migrated in the microchannel by the application of a centrifugal force. If the function of platelet is normal, the flow path in the microchannel is clogged in a short time and then the flow is stopped or the migration distance is short. On the contrary, if the function of platelet is abnormal, the time for clogging is lengthened or the migration distance is increased compared to when the function of a platelet is normal.

Regarding the test of a drug tolerance, in particular when aspirin, clopidogrel, ticlopidine, etc is taken, the aggregation function of platelet is decreased. Therefore, the flow path in the microchannel is not clogged easily so that the clogging time is increased and the migration distance is also increased. Since a normal person reacts to the drug well, the clogging time is short. If the ratio of the clogging time is decreased remarkably compared to a normal person, it is determined to be the drug tolerance to aspirin and clopidogrel.

Hereinafter, an apparatus for testing a multi-function and a drug response of platelet based on a centrifugal microfluidics according to another embodiment of the present invention will be described.

Figure 5:
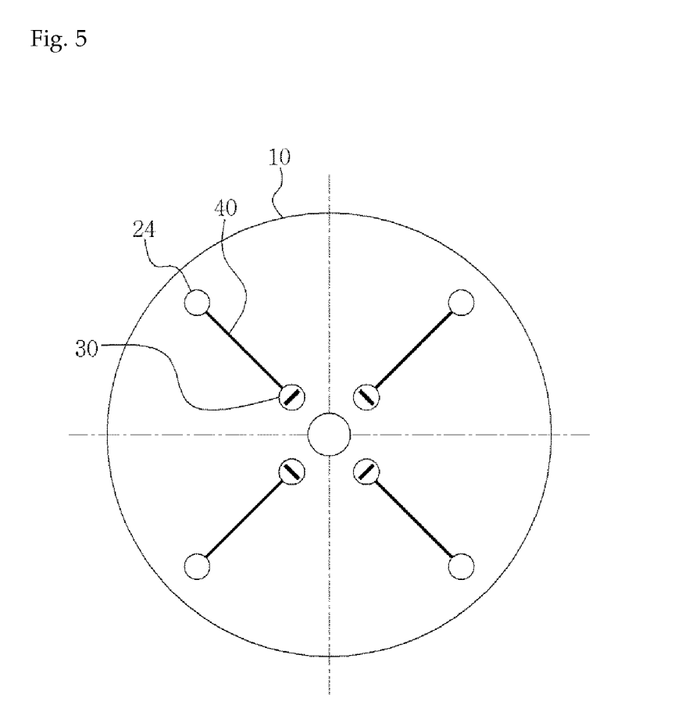
FIG. 5 shows an apparatus for testing a multi-function and a drug response of a platelet based on a centrifugal microfluidics according to another embodiment of the present invention.

FIG. 5 shows an arrangement of an apparatus for testing a multi-function and a drug response of a platelet based on a centrifugal microfluidics according to another embodiment of the present invention.

Referring to the figure, in the embodiment, it is advantageous that the test for four different blood samples can be carried out with a single test by introducing four different blood samples into a single disk 10. In the embodiment, the stirring chamber 30 also functions as a sample chamber to contain blood sample. That is, the stirring chamber in this embodiment is configured to act as both the sample chamber 20 and the stirring chamber 30 in FIG. 1. The number of the stirring chamber 30 is not limited to four as shown in the figure. For example, a plurality of stirring chambers 30 and microchannels 40 having the same number of the stirring chambers can be provided to enable a test for a plurality of blood samples. Here, a plurality of stirring chambers 30 can be arranged circumferentially on the center of the disk 10 and blood samples introduced into each stirring chamber 30 can migrate radially, respectively.

Further, the microchannel 40 may have at least one of a straight shape, a curved shape, zigzags shape, etc., or the combination thereof.

Hereinafter, a method for testing a multi-function and a drug response of a platelet based on a centrifugal microfluidics having the above feature will be described in detail.

Figure 6:
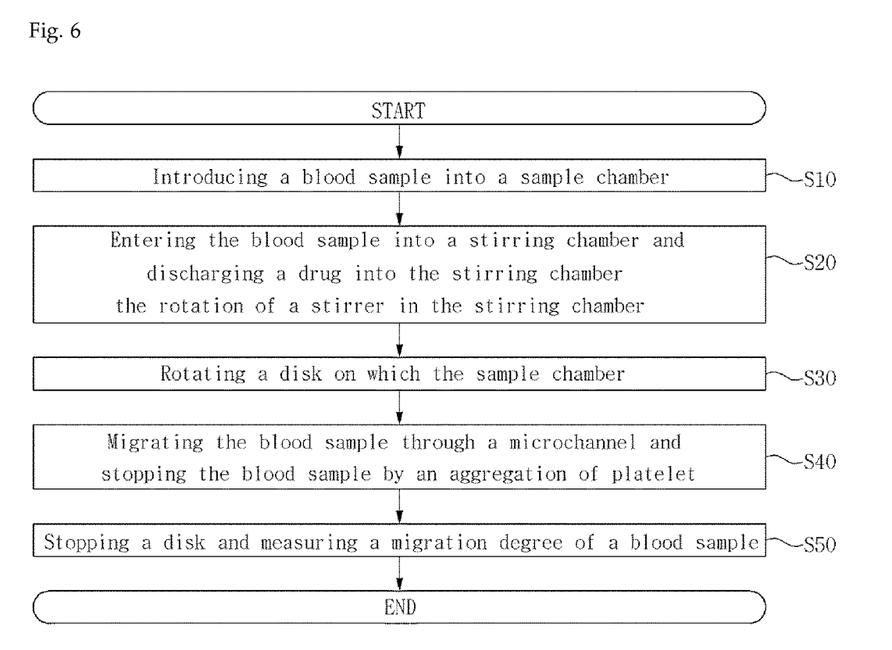
FIG. 6 is a flow diagram of a method for testing a multi-function and a drug response of a platelet based on a centrifugal microfluidics according to one embodiment of the present invention.

FIG. 6 is a flow diagram of a method for testing a multi-function and a drug response of a platelet based on a centrifugal microfluidics according to one embodiment of the present invention.

As shown in the figure, a tester introduces a blood sample collected by venipuncture into the sample chamber 20 (S10). Then, the blood sample is introduced into a stirring chamber 30 through the connection channel 22 connected to the sample chamber 20 and the stirrer 32 in the stirring chamber 30 rotates by an electromagnetic force such that the drug 34 in the stirrer 32 is discharged and is mixed with the blood sample (S20).

Here, in case of an activation test by a mechanical stimulus to a platelet, the fast rotation at a specific rpm enables the activation of platelet and von Willebrand factor (vWF). If not for the mechanical activation test, the rotation can be carried out at a predetermined speed during a predetermined time for the purpose of stirring the drug and the blood sample.

Then, the disk 10 on which the sample chamber 20 is installed rotates (S30). Thereafter, if the microfluidic valve 42 is opened, the blood sample migrates downstream through the microchannel 40. The migration rate and distance differ depending on the aggregation degree and the adhesion degree and the blood sample stops or migrates to the end (S40).

Then, the disk 10 stops and the migration degree of the sample is measured by a measuring part 50 such as a video device, a light source and a light-detecting sensor, etc. (S50).

As a method of activating a platelet by applying a shear stress to the blood sample, besides the method of generating a shear flow by the rotation of the stirrer, a platelet can be activated with a high shear flow of blood by a centrifugal force. In more detail, the rotation speed is increased to a predetermined value while the microfluidic valve 42 is being closed after the blood sample is introduced. Thereafter, if the microfluidic valve 42 is opened, a high shear flow occurs through the microchannel 40. A platelet which is activated therethrough reacts to a drug such as an agonist which is coated on the expansion part 46 or a specific portion. This reaction causes the aggregation and adhesion which results in the interruption of the progress of flow. Here, a drug response test can be carried out by the migration ratio of the sample flow, the time to reach the end of the microchannel 40, etc.

The scope of the present invention is not limited to the above described embodiments and is determined by the accompanying claims. It is apparent that various variations or modifications can be made within the scope of the claims by those skilled in the art.

LIST OF REFERENCE NUMERALS

10: disk
20: sample chamber
22: connection channel
30: stirring chamber
32: stirrer
34: drug
36: seal
40: microchannel
42: microfluidic valve
44: intermittent chamber
46: expansion part
50: measuring part

The invention claimed is:

1. An apparatus for testing based on centrifugal microfluidics comprising:
   a rotatable disk;
   a sample chamber which is located on the disk and which is configured to contain a blood sample therein;
   a stirring chambers configured to receive the blood sample and to induce a shear flow in the blood sample;
   a microchannel which is connected to the stirring chambers and in which platelet aggregation and adhesion occur during a migration of the blood sample;
   a waste sample chamber configured to receive the blood sample which passed the microchannel; and
   a sensor which is installed on the disk and which is configured to measure a migration distance of the blood sample according to clogging of the microchannel due to the platelet aggregation and adhesion that occurs during the migration of the blood sample.

2. The apparatus according to claim 1, wherein the sample chamber circumscribes the center of the disk.

3. The apparatus according to claim 1, wherein a stirrer is rotatably installed in the stirring chamber.

4. The apparatus according to claim 3, wherein the stirrer is shaped in the form chosen from a straight cylindrical bar, a cross cylindrical bar and a circular plate.

5. The apparatus according to claim 3, wherein a drug which activates or inactivates aggregation of a platelet is contained in the stirrer in a liquid or solid state.

6. The apparatus according to claim 5, wherein the drug is at least one agonist chosen from collagen, adenosine diphosphate (ADP) and epinephrine.

7. The apparatus according to claim 5, wherein the drug is at least one antagonist chosen from aspirin, P2Y1 receptor antagonist and P2Y12 receptor antagonist.

8. The apparatus according to claim 7, wherein the P2Y1 receptor antagonist is at least one chosen from MRS 2179, MRS 2279, MRS 2500, A2P5P, A3P5P and A3P5PS.

9. The apparatus according to claim 7, wherein the P2Y12 receptor antagonist is at least one chosen from clopidogrel, ticlopidine, prasugrel, AR-C67085MX, cangrelor, C1330-7, MRS 2395 and 2-methylthioadenosine-5'-monophosphate.

10. The apparatus according to claim 3, wherein the stirring chamber and stirrer are configured to generate a minimum shear rate of at least 5,000 $(s^{-1})$ or a minimum shear stress of at least 8 Pa.

11. The apparatus according to claim 3, wherein the stirrer comprises openings at a center portion and at a plurality of ends, and the openings are each provided with a seal.

12. The apparatus according to claim 11, wherein the seal is a phase-change material or an aqueous membrane.

13. The apparatus according to claim 12, wherein the seal is a paraffin wax or a starch.

14. The apparatus according to claim 1, wherein a microfluidic valve is installed in the front part of the microchannel to control the flow of the blood sample.

15. The apparatus according to claim 1, wherein the microchannel is shaped in the form of at least one of a straight line, a curve or a zigzag, or the combination thereof.

16. The apparatus according to claim 1, wherein a plurality of intermediate chambers are formed at a plurality of points in the microchannel.

17. The apparatus according to claim 1, wherein the microchannel is provided with a series of expansion parts that are configured to have widths greater than the width of the microchannel and sufficient to simulate a physiological pulsed pressure and shear stress when the blood sample is under centrifugal force.

18. The apparatus according to claim 1, wherein the stirring chamber is connected to the sample chamber in a configuration distal to the sample chamber from the center of the disk.

19. The apparatus according to claim 1, wherein the microchannel has a surface prepared to increase platelet adhesion.

* * * * *